United States Patent

Korber et al.

[11] 4,192,321
[45] Mar. 11, 1980

[54] TOOTH DISPLACEMENT MEASURING APPARATUS

[76] Inventors: Elmar Körber, Adolf-Bechlerstrasse 15, D-7501 Malsch; Heinz Dehnert, Grunstrasse 1 a, D-7801 Hugstetten-March, both of Fed. Rep. of Germany

[21] Appl. No.: 923,866

[22] Filed: Jul. 12, 1978

[30] Foreign Application Priority Data

Jul. 22, 1977 [DE] Fed. Rep. of Germany ....... 2733081

[51] Int. Cl.$^2$ .............................................. A61B 5/10
[52] U.S. Cl. .................................................. 128/776
[58] Field of Search ......................... 128/774, 776, 777

[56] References Cited

U.S. PATENT DOCUMENTS

| | | | |
|---|---|---|---|
| 3,782,188 | 1/1974 | Korber et al. | 128/776 |
| 3,883,954 | 5/1975 | Simmering et al. | 128/776 |
| 3,943,913 | 3/1971 | Johnson | 128/776 |
| 4,058,115 | 11/1977 | Forster | 128/776 |

Primary Examiner—William E. Kamm
Attorney, Agent, or Firm—Pollock, Vande Sande & Priddy

[57] ABSTRACT

An improved tooth displacement measuring apparatus for measuring the displacement of a test tooth in response to particular applied forces. A zero value selector automatically adjusts the measured values of tooth displacement with respect to a reference calibration displacement defined by the displacement measured in response to a calibration force. The measured values of displacement corresponding to the particular applied forces are stored and selectively displayed.

8 Claims, 3 Drawing Figures

TOOTH DISPLACEMENT MEASURING APPARATUS

BACKGROUND OF THE INVENTION

The invention relates to an improved tooth displacement measuring apparatus and, more particularly, to such an apparatus including circuitry adapted to provide an automatic zero-displacement adjustment for measured values of tooth displacement and for storing and later displaying measured values of tooth displacement corresponding to particular values of applied force.

When examining the condition of teeth, it is often useful to determine the degree of movement of individual teeth in response to applied force, since the degree of loosening of a tooth provides an indication of the existence of or the extent of the decay of the tooth-accomodating bone and of the tooth-supporting structure. Accordingly, tooth displacement measuring devices have been devised to apply increasing pressure on the tooth under examination and to measure the resulting relative displacement of the tooth with respect to adjacent teeth.

More particularly, devices employing three calipers or measuring rods are known to the art. In such devices, a force transmitting rod is supported within a housing by a force spring. The rod extends outside of the housing and its free end is adapted to be attached to a test tooth. Two displacement measuring rods are typically positioned adjacent the force transmitting rod and are supported within the housing by respective weak restoring springs that are adapted to apply a weak counter restoring force in response to axial forces applied to the rods.

In operation, the free end of the force transmitting rod is affixed to the test tooth and the ends of the displacement measuring rods are positioned to abut adjacent teeth. The housing is then pressed manually in a forward direction and the force transmitting rod is thereby caused to apply increasing pressure on the test tooth.

The applied force is measured by a force transducer that is attached to the force transmitting rod. The transducer is typically used to measure the force acting upon the force spring.

As pressure is applied to the test tooth, position sensing transducers on the displacement measuring rods register the relative displacement between the respective displacement measuring rods and the force transmitting rod.

Thus, such a prior art device is adapted to measure the relative displacement of a test tooth with respect to adjacent reference teeth in response to applied force.

However, in order to display the force and displacement measurements taken by such prior art devices, it has been necessary to utilize a relatively complicated twinchannel recorder that plots curves corresponding to the applied force and the resultant tooth displacement. Typically, the data plots are then used to prepare a force-displacement graph that describes the displacement characteristics of the tooth. Such an analysis of the tooth displacement data is not only expensive and time consuming but is also better adapted to use in scientific institutions than in a dentist's office.

It has been suggested that the tooth displacement data analysis may be simplified by plotting the displacement curve and superimposing on this curve the peaks that arise when the force acting on the tooth is increased by a particular amount. However, it has been determined that the evaluation of even such a simplified curve is a tedious operation that would probably not be suitable to a practicing dentist.

In addition, a further disadvantage of the prior art is that a displacement measuring device must be adjusted to a zero displacement reading after it is engaged with the test tooth and reference teeth, since the displacement measuring rods will initially be deflected slightly from their zero force positions, even though no force is being exerted on the test tooth.

It should be appreciated that not only is such an initial calibration adjustment time consuming, but also the adjustment is difficult to execute since the housing of the device must be held very steadily to avoid additional movement of the displacement rods.

Practical tests have shown that a satisfactory, quantitative evaluation of tooth displacement may be obtained if tooth displacement is measured at particular values of applied force. For example, it has been determined that it is sufficient to measure tooth displacement at forces of 100 pond and 500 pond applied perpendicular to the axis of the tooth and in both the palatal or compression stress and labial or tensile stress directions.

Accordingly, it is an object of the invention to provide a simple and effective means to measure tooth displacement in response to particular values of applied force.

A further object of the invention is to provide an apparatus to automatically apply a zero displacement adjustment to measured values of displacement.

Another object of the invention is to provide a simple means to store and display measured displacement values.

These and other objects of this invention will become apparent from a review of the detailed specification which follows and a consideration of the accompanying drawings.

BRIEF SUMMARY OF THE INVENTION

In order to achieve the objects of the invention and to overcome the problems of the prior art, the improved tooth displacement measuring apparatus, according to the invention, includes means to automatically apply a zero-displacement adjustment to measured values of tooth displacement and to store and display the adjusted displacement values.

More particularly, an embodiment of the invention includes a force transducer that generates an applied force signal that corresponds to the force applied by a force transmitting rod to a test tooth. As the test tooth moves in response to the increasing force, displacement measuring rods, positioned to abut adjacent teeth, are displaced with respect to the force transmitting rod and displacement measuring transducers generate displacement signals corresponding to the respective relative displacements of the displacement rods.

The displacement signals are averaged by an averaging circuit to produce an average displacement signal corresponding to the average displacement of the displacement rods from the force transmitting rod.

A zero-value selector circuit subtracts a calibration displacement signal, corresponding to the average displacement measured in response to an initial small calibration force, from average displacement signals generated in response to applied forces in excess of the calibration force.

A plurality of reference force selectors are adapted to respond to selected values of force to generate corresponding reference force signals.

The reference force signal of each reference force selector is applied to a corresponding pair of comparators that also receive the applied force signal. One of the comparators of a comparator pair responds to applied labial force signals to generate a hold signal when the force signal equals the comparator's associated reference force signal. The other comparator of a comparator pair responds to applied palatal force signals to generate a hold signal when the force signal equals the comparator's associated reference force signal.

Each comparator is connected to a sample and hold circuit that responds to the comparator's particular hold signal to store the average displacement signal present when the hold signal is generated.

A display means is provided to display the stored contents of selected sample and hold circuits. In addition, indicator lamps may be provided to respond to the generation of hold signals by the comparators to indicate that a particular displacement measurement has taken place.

DETAILED DESCRIPTION OF PREFERRED EMBODIMENTS

Figure 1:
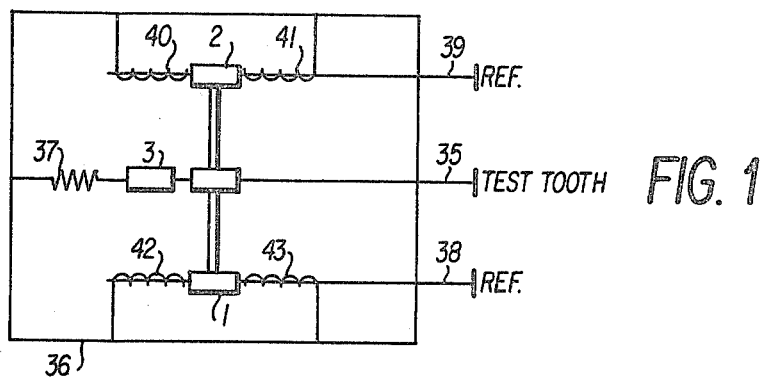
FIG. 1 shows a diagram of the force transmitting and displacement measuring apparatus of the invention.

The remaining portion of this specification will describe preferred embodiments of the invention when read in conjunction with the attached drawings, in which like reference characters identify identical apparatus.

FIG. 1 illustrates the structure of a tooth displacement measuring apparatus in accord with a preferred embodiment of the invention. More particularly, the apparatus includes a central force transmitting rod 35 that is supported inside a housing 36 by a spring 37. The force transmitting rod 35 passes through a hole disposed in a face of the housing 35 and is adapted to be attached at its free end to a particular test tooth in a manner known to the art. A force transducer 3 is attached to the force transmitting rod 35 to measure the magnitude of any force that is applied through the rod to act upon the spring 37.

A displacement measuring rod 39 passes through a hole in the face of the housing 36 and is supported within the housing 36 by two opposing relatively weak restoring springs 40 and 41. The restoring springs 40 and 41 are adapted to apply a weak counter restoring force in response to axial forces applied to the displacement measuring rod 39. Likewise, relatively weak restoring springs 42 and 43 support a displacement measuring rod 38 and provide a similar weak restoring force in response to axial forces on the rod 38.

The displacement rods 38 and 39 have respective position sensors 1 and 2 that are adapted to measure the relative shift in position between the force transmitting rod 35 and the displacement measuring rods 38 and 39.

It should be appreciated that the above described elements of a tooth displacement measuring apparatus are known to the art and are particularly described, for example, in a published German Patent Application OS No. 21 62 683.

In operation, the force transmitting rod 35 is affixed to the tooth to be tested and the ends of the displacement measuring rods 38 and 39 are positioned to abut adjacent teeth and are held in place by the weak restoring spring force of the springs 40–43. A force, for example a pressing force, is applied to the housing and the pressing force is transmitted to the test tooth through the spring 37 and the force transmitting rod 35.

It should be apparent that if the test tooth yields to the pressing force applied through the force transmitting rod 35, the displacement measuring rods 38 and 39 will be displaced in a direction opposite to the direction of the applied pressing force and the position measuring transducers 1 and 2 will measure the magnitude of the shift in position.

It should be apparent that the tooth displacement measuring apparatus of FIG. 1 will operate in a similar fashion to register the displacement of a test tooth if a pulling force is applied to the apparatus.

Figure 2:
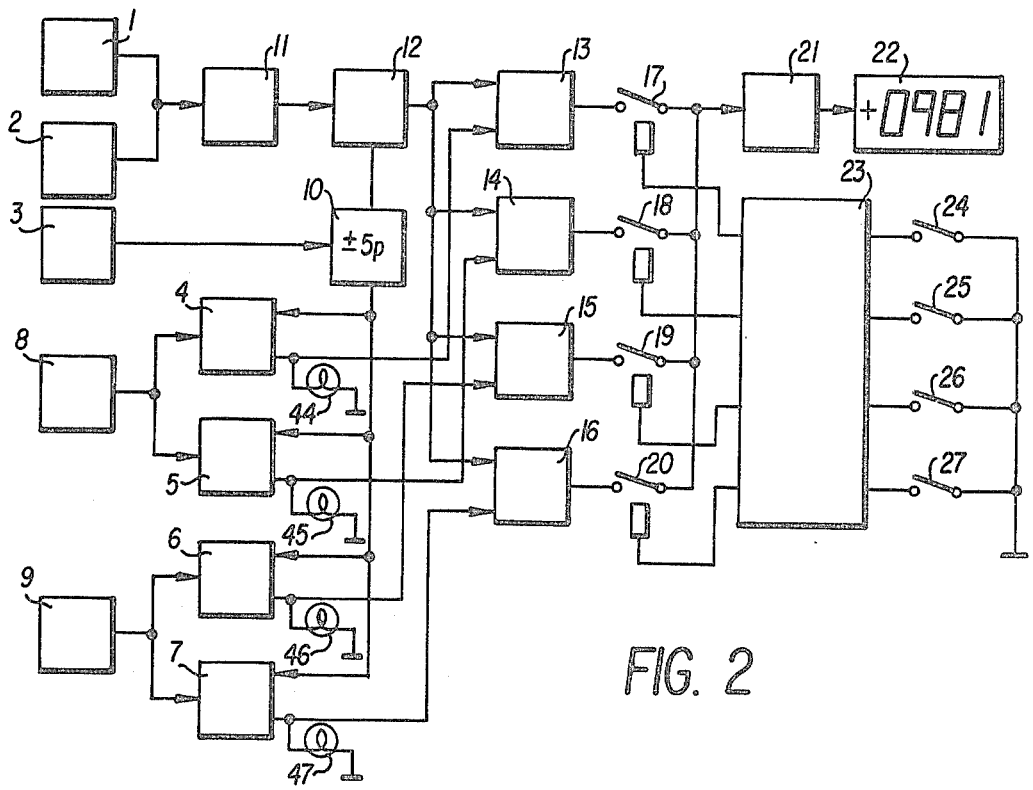
FIG. 2 shows a block diagram of a tooth displacement measuring circuit in accordance with an embodiment of the invention.

In accordance with the invention, the apparatus of FIG. 1 cooperates with a tooth displacement measuring circuit illustrated in FIG. 2, to automatically measure the displacement of a test tooth in response to particular values of applied force. In the circuit, a force pre-selector switch 8 is connected to comparators 4 and 5 and the comparators are respectively connected to sample and hold circuits 13 and 14. Likewise, a second force pre-selector switch 9 is connected to comparators 6 and 7 and the comparators are respectively connected to sample and hold circuits 15 and 16.

The force transducer 3 is connected to the comparators 4–7 and to a trigger device 10. The trigger device 10 is connected to a zero point selector 12 that is in turn connected to each of the sample and hold circuits 13–16.

The displacement transducers 1 and 2 are connected to an averaging circuit 11, which is connected to the zero point selector 12.

The outputs of the sample and hold circuits 13–16 may be selectively connected by the display switches 17–20 to an analog-digital converter 21 that is in turn connected to a digital display 22. The switches 17–20 can be separately actuated in a manner known to the art by a control circuit 23 cooperating with switch select keys 24–27. Thus, activation of a particular switch select key will cause the control circuit 23 to apply an activation voltage to a corresponding relay to close a particular display switch. Likewise, deactivation of a switch select key will de-energize an associated relay to open a corresponding display switch. It should be appreciated that the switches 17–20 could be solid state devices, for example transistors, responsive to activation voltages of the control circuit 23 to conduct and responsive to a de-activation condition of the control circuit to switch to a non-conducting state.

In operation, the force transmitting rod 35 is attached to the test tooth and the displacement measuring rods 38 and 39 are placed in abutting relation to adjacent teeth and held in place by a weak restoring spring force. The pre-selector switch 8 is then set to a first value of force, for example 100 pond, at which the tooth displacement is to be measured. The second pre-selector switch 9 is set to a second value of force, for example 500 pond, and the housing 36 is moved in a palatal direction to apply an increasing compression stress at right angles to the axis of the test tooth. When the force transducer 3 measures an applied force just exceeding a positive threshold, for example 5 pond, the trigger circuit 10 is activated and the zero-point selector 12 is thereby enabled to automatically calibrate the circuit of FIG. 2 to zero displacement and zero force.

Figure 3:
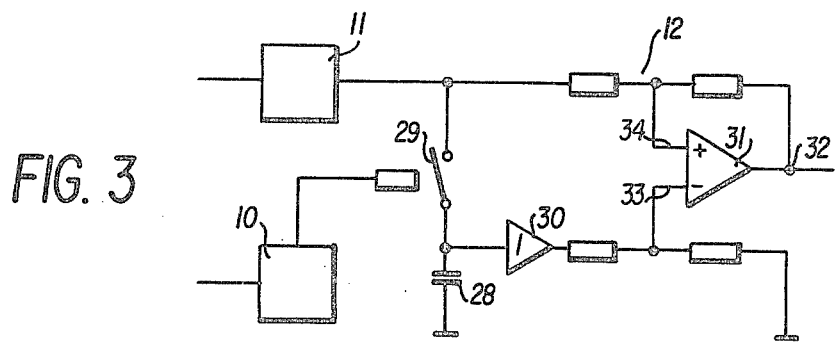
FIG. 3 shows a circuit diagram of the zero-point selector of the circuit of FIG. 2.

FIG. 3 more particularly illustrates the operation of the zero-point selector 12 in accord with an embodiment of the invention. In operation, as force is applied to the test tooth the displacement transducers 1 and 2 generate voltages corresponding to the displacement of the rods 38 and 39. The averaging circuit 11 averages these displacement voltages in a manner known to the art and generates an average displacement voltage that is applied to the zero-point selector circuit 12 of FIG. 3. In the circuit 12 a switch 29, for example a solid state switch or a relay operated switch, is closed and a capacitor 28 is thereby charged to a voltage corresponding to the average displacement voltage of the averaging circuit 11. Thus, the voltage charge on the capacitor 28 is proportional to the average displacement measured by the displacement transducers 1 and 2.

As the force applied to the tooth increases, the voltage applied by the force transducer 3 at the input of the trigger circuit 10 also increases until the trigger circuit is activated at a level of applied force of 5 pond. The activation of the trigger circuit 10 causes the solid state switch 29 to open and thereby causes the capacitor 28 to stop charging.

Thus, the opening of the switch 29 isolates a "calibration voltage" on the capacitor 28 that is proportional to the average displacement of the measuring rods 38 and 39 at the time that a calibrating force of 5 pond is applied to the test tooth. The calibration voltage at the capacitor 28 is applied to an input of an electrometer amplifier 30 with a unity gain, and the output of the amplifier 30 is applied to an input 33 of a differential amplifier 31.

The output of the averaging circuit 11 is applied to another input 34 of the differential amplifier 31 and the resultant voltage at the output 32 of the amplifier 31 is proportional to the difference between the average displacement voltage of the circuit 11 and the calibration voltage of the capacitor 28. Thus, as force in excess of 5 pond is applied to the test tooth, the output 32 registers the magnitude of the displacement of the test tooth from an initial calibration position that is defined by the voltage on the capacitor 28.

It should be appreciated that the automatic zero-point selector circuit 12 of FIG. 3 renders the manual calibration positioning adjustment of the measuring apparatus unnecessary since the circuit automatically corrects for the effect of the initial positioning of the displacement measuring rods 38 and 39 with respect to the force transmitting rod 35.

As the applied force increases past the 5 pond calibration level, the comparator 4 compares the output of the force transducer 3 with the pre-selected force input of the switch 8. When the force directed on the test tooth, as measured by the force transducer 3, is equal to the pre-selected force, the comparator 4 generates a hold signal that is applied to the sample and hold circuit 13. The sample and hold circuit 13 responds to the hold signal to store the instantaneous calibrated value of tooth displacement that exists at the output 32 of the differential amplifier 31 of the zero-point selector 12.

For example, if the pre-selector switch 8 is operated to generate a voltage corresponding to a force of 100 pond and increasing palatal force is applied to the test tooth, the comparator 4 will generate a hold signal to store a value of tooth displacement in the sample and hold circuit 13 when a palatal force of 100 pond is applied to the test tooth.

Furthermore, when the palatal force increases to a point defined by the pre-selector switch 9, for example 500 pond, the comparator 6 will generate a hold signal to store a corresponding value of tooth displacement in the sample and hold circuit 15.

The tooth displacement test is continued by pulling the apparatus of the invention away from the test tooth and thereby applying a tensile force in the labial direction. When the force transducer 3 generates a voltage corresponding to the negative threshold level of 5 pond applied in the labial direction, the trigger circuit 10 will be activated, the zero-point selector circuit 12 will be operated to apply a fixed calibration voltage to an input 33 of the differential amplifier 31, and the output 32 of the amplifier 31 will register zero displacement.

As the increasing labial force reaches a value of 100 pond, the comparator 5 will generate a hold signal to store the instantaneous value of tooth displacement in the sample and hold circuit 14. Likewise, when a force of 500 pond is applied in the labial direction, the comparator 7 will generate a hold signal to store the corresponding, instantaneous value of tooth displacement in the sample and hold circuit 16.

The force values that were stored in the sample and hold circuits 13–16 may be successively recalled and displayed on the display device 22 by manually activating the keys 24–27. It should be apparent that successive activation of the keys 24–27 will successively show the values of tooth displacement corresponding to applied palatal and labial forces of 100 pond and palatal and labial forces of 500 pond.

The preferred embodiment of the invention may include 4 small lamps 44–47 disposed on a face of the housing 36 and adapted to successively light up as each of the four selected displacement measurements are completed. Thus, the operator will have a positive indication of the completion of the measurements without having to closely monitor the apparatus.

It should be understood that the indicator lamps may be connected to the outputs of the comparator circuits 4–7 to indicate when the comparators have been activated and to thereby provide an indication of the completion of the measuring operations. In addition, it should be appreciated that the operation of the apparatus of the invention is not limited to particular values of applied force, although research has indicated that displacement measurements at forces of 100 and 500 pond in the palatal and labial directions are effective to define the displacement characteristics of a tooth.

Moreover, the invention is not limited to a particular number of displacement measuring rods, since any number of rods can be used to determine respective relative displacements from an initial calibrated position with respect to a force transmitting rod. Also, it should be understood that the circuit of FIG. 2 can include any number of pre-selectors and associated comparators and sample and hold circuits without departing from the spirit of the invention.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is:

1. In a tooth displacement measuring apparatus of a type wherein a force transmitting member applies force to a test tooth and at least one displacement member abuts a reference surface to define a zero force reference position to measure the relative displacement of said displacement member from said force transmitting member in response to said force, the improvement comprising:
   force measuring means for generating an applied force signal corresponding to the force applied by said force transmitting member to said test tooth;
   displacement measuring means for generating a displacement signal corresponding to the relative displacement between said force transmitting member and at least one displacement member;
   reference force selector means for generating reference signals corresponding to selected values of force;
   at least one comparator for comparing said applied force to at least one reference signal and generating an associated hold signal when the reference signal is equal to the applied force signal; and
   at least one sample and hold circuit, operatively connected to a corresponding comparator and responsive to the hold signal of the comparator to store a displacement signal.

2. The apparatus of claim 1 wherein a plurality of comparators cooperate in groups of two to receive a particular reference signal and said applied force signal, and one comparator of each group operates to generate a hold signal in response to a match between said particular reference signal and an applied force signal corresponding to a force applied in one direction and the other comparator of each group operates to generate a hold signal in response to a match between said particular reference signal and an applied force signal corresponding to a force applied in an opposite direction.

3. The apparatus of claim 1 further comprising a zero-value selector means for subtracting a calibration displacement signal measured by said displacement measuring means in response to a particular calibration force, from the displacement signals generated in response to increasing force to derive resultant zero force adjustment displacement signals.

4. The apparatus of claim 3 wherein said zero value selector means includes:
   a triggering means for responding to said particular calibration force to generate a calibration hold signal;
   a storage means responsive to said calibration hold signal to store said calibration displacement signal; and
   a subtracting means for subtracting the stored calibration displacement signal from displacement signals generated in response to applied forces in excess of said particular calibration force.

5. The apparatus of claim 1 wherein said displacement measuring means includes an averaging circuit for averaging the relative displacements of a plurality of displacement members from said force transmitting member and generating a displacement signal corresponding to the average relative displacement of said displacement members from said force transmitting member.

6. The apparatus of claim 1 further comprising indicator means for providing a perceptible signal in response to the generation of hold signals by said comparators.

7. The apparatus of claim 6 wherein said indicator means includes a plurality of signal lamps that are energized in response to the generation of hold signals by said comparators.

8. The apparatus of claim 1 further comprising a display means for displaying the value of the displacement signals stored in the sample and hold circuits.